United States Patent [19]

Downing et al.

[11] Patent Number: 5,486,517
[45] Date of Patent: Jan. 23, 1996

[54] BENZIMIDAZOLES AND IMIDAZOPYRIDINES AS CENTRAL NERVOUS SYSTEM AGENTS

[75] Inventors: Dennis M. Downing; Shelly A. Glase; Stephen J. Johnson; Lawrence D. Wise; Jonathan L. Wright, all of Ann Arbor, Mich.

[73] Assignee: Warner-Lambert Company, Morris Plains, N.J.

[21] Appl. No.: 240,355

[22] Filed: May 10, 1994

[51] Int. Cl.$^6$ ............ A61K 31/495; A61K 31/505; C07D 403/10; C07D 403/12

[52] U.S. Cl. ............ 514/253; 514/256; 514/303; 514/338; 544/295; 544/362; 544/364; 544/370; 544/333; 544/392; 546/118; 546/271; 548/309.7; 548/310.1

[58] Field of Search ............ 544/362, 370, 544/295, 364; 514/253

[56] References Cited

U.S. PATENT DOCUMENTS 3,985,891  10/1976  Kutter et al. ............ 514/303

FOREIGN PATENT DOCUMENTS 56866    8/1982  European Pat. Off. ............ 544/370
2305339  8/1974  Germany .
2361757  6/1975  Germany .

OTHER PUBLICATIONS

Kutter et al., *Chemical Abstracts*, vol. 82, No. 4251 (1974).

Hasegawa et al., *Chemical Abstracts*, vol. 75, No. 76797 (1971).

Kutter et al., Chemical Abstracts, vol. 83, No. 206270 (Abstract for DE 2,361,757 Jun. 26, 1975 (1975).

*Primary Examiner*—Emily Bernhardt
*Attorney, Agent, or Firm*—Francis J. Tinney

[57] ABSTRACT

Benzimidazoles and imidazopyridines are described, as well as methods for the preparation and pharmaceutical composition of same, which are useful as central nervous system agents and are particularly useful as antipsychotic agents and for the treatment of disorders which respond to dopaminergic blockade including psychotis depression, substance abuse, and compulsive disorders.

5 Claims, No Drawings

BENZIMIDAZOLES AND IMIDAZOPYRIDINES AS CENTRAL NERVOUS SYSTEM AGENTS

BACKGROUND OF THE INVENTION

The present invention relates to novel substituted benzimidazoles and imidazopyridines useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are dopaminergic agents useful as antipsychotic agents for treating psychoses such as schizophrenia.

Dopamine D2 antagonists are established as antipsychotic agents. More recently, the dopamine D3 receptor has been identified (Schwartz Jean-Charles, et al., The Dopamine D3 Receptor as a Target for Antipsychotics. In *Novel Antipsychotic Drugs*, Meltzer H. Y., Ed., Raven Press, New York, 1992, p. 135–144). On the basis of the localization of the dopamine D3 receptor in the limbic area of the brain, a selective D3 antagonist should show antipsychotic activity but not have the neurological side effects of D2 antagonists (Sokoloff P., et al., Molecular Cloning and Characterization of a Novel Dopamine Receptor ($D_3$) as a Target for Neuroleptics, *Nature*, 347:146 (1990); Sokoloff P., et al., Localization and Function of the $D_3$ Dopamine Receptor, *Arzneim.-Forsch./Drug Res.*, 42(1):224, (1992)).

The compounds of the present invention are also useful for the treatment of disorders which respond to dopaminergic blockade which include psychotic depression, substance abuse (Caine S. B. and Koob G. F., Modulation of Cocaine Self-Administration in the Rat Through D-3 Dopamine Receptors, *Science*, 260:1814 (1993)), and compulsive disorders (Goodman W. K., et al., The role of serotonin and dopamine in the pathophysiology of obsessive compulsive disorder, *International Clinical Psychopharmacology*, 7(Supp. 1):35 (1992)).

We have surprisingly and unexpectedly found that a series of benzimidazoles and imidazopyridines are dopaminergic agents which bind selectively to the dopamine D3 receptor and are thus useful as antipsychotic agents for treating psychoses such as schizophrenia.

SUMMARY OF THE INVENTION

Accordingly, the present invention is a compound of Formula I

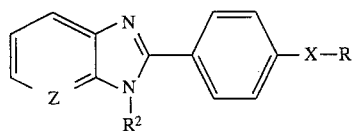

wherein R is

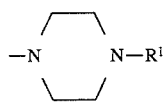

wherein $R^1$ is aryl, or heteroaryl, or

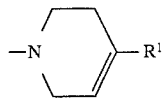

wherein $R^1$ is as defined above;
$R^2$ is hydrogen, or
alkyl of from 1 to 6 carbon atoms;
X is -Y-$(CH_2)_n$-
wherein Y is O, S or NH, and n is an integer from 2 to 5,

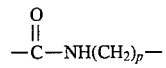

wherein p is an integer from 1 to 4,

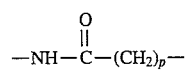

wherein p is as defined above,
alkyl of from 3 to 6 carbon atoms,
alkenyl of from 3 to 6 carbon atoms,
alkynyl of from 3 to 6 carbon atoms;
Z is N or CH;
and corresponding isomers thereof; or a pharmaceutically acceptable acid addition salt thereof.

As dopaminergic agents selective for the dopamine D3 receptor subtype, the compounds of Formula I are useful as antipsychotic agents for treating psychoses such as schizophrenia. They are also useful for the treatment of disorders which respond to dopaminergic blockade. Thus, Other embodiments of the present invention include the treatment, by a compound of Formula I, of psychotic depression, substance abuse, and compulsive disorders.

A still further embodiment of the present invention is a pharmaceutical composition for administering an effective amount of a compound of Formula I in unit dosage form in the treatment methods mentioned above. Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "alkenyl" means a straight or branched unsaturated hydrocarbon radical having from 3 to 6 carbon atoms and includes, for example, 2-propenyl, 1-butenyl, 2-butenyl, 1-pentenyl, 2-pentenyl, 3-methyl-3-butenyl, 1-hexenyl, 2-hexenyl, 3-hexenyl, and the like.

The term "alkynyl" means a straight or branched triple bonded unsaturated hydrocarbon radical having from 3 to 6 carbon atoms and includes, for example, 2-propynyl, 1-butynyl, 2-butynyl, 3-butynyl, 1-pentynyl, 3-pentynyl, 1-hexynyl, 2-hexynyl, 3-hexynyl, and the like.

"Alkoxy" and "thioalkoxy" are O-alkyl or S-alkyl of from 1 to 6 carbon atoms as defined above for "alkyl".

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, or 1,3-benzodioxol-5-yl.

The term "heteroaryl" means a heteroaromatic radical which is 2-, 3-, or 4-pyridinyl, 2-, 4-, or 5-pyrimidinyl, or 2-, or 3-thienyl.

"Halogen" is fluorine, chlorine, bromine, or iodine.

"Alkali metal" is a metal in Group IA of the periodic table and includes, for example, lithium, sodium, potassium, and the like.

The compounds of Formula I are capable of further forming pharmaceutically acceptable acid addition salts. These forms are within the scope of the present invention.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts", *Journal of Pharmaceutical Science*, 66:1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention may exist as a mixture of cis and trans isomers or as the individual cis and trans isomers. The mixture of isomers as well as the individual isomers are intended to be encompassed within the scope of the present invention.

A preferred compound of Formula I is one wherein R is

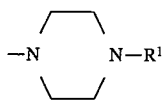

wherein $R^1$ is aryl, or heteroaryl, or

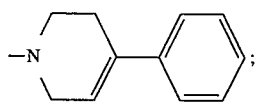

$R^2$ is hydrogen, methyl, or ethyl;
X is -Y- $(CH_2)_n$-
wherein Y is O or NH and n is an integer from 3 to 4,

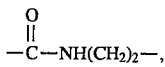

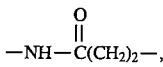

butyl,
butenyl, or
butynyl;
Z is N or CH;
and corresponding isomers thereof; or a pharmaceutically acceptable acid addition salt thereof.

Particularly valuable are:
2-[4-[3-(4-Phenyl-1-piperazinyl)propoxy]phenyl]-1H-benzimidazole;
2-[4-[3-[4-(2,3-Dichlorophenyl)-1-piperazinyl]-propoxy]phenyl]-1H-benzimidazole;
2-[4-[3-[4-(2-Pyridinyl)-1-piperazinyl-propoxy]phenyl]-1H-benzimidazole;
2-[4-[3-[4-(2-Pyrimidinyl)-1-piperazinyl]-propoxy]-phenyl]-1H-benzimidazole;
2-[4-[3-[4-(4-Methylphenyl)-1-piperazinyl]-propoxy]phenyl]-1H-benzimidazole;
2-[4-[3-[4-(4-Fluorophenyl)-1-piperazinyl]-propoxy]phenyl]-1H-benzimidazole;
2-[4-[3-[4-[2-(Propylthio)phenyl]-1-piperazinyl]-propoxy]phenyl]-1H -benzimidazole;
2-[4-[3-(3,6-Dihydro-4-phenyl-1(2H)-pyridinyl)propoxy]phenyl]-1H-benzimidazole;
2-[4-[3-[4-(4-Chlorophenyl)-1-piperazinyl]-propoxy]phenyl]-1H-benzimidazole;
2-[4-[3-[4-(2 -Methoxyphenyl)-1-piperazinyl]-propoxy]phenyl]-1H-benzimidazole;
2-[4-[3-[4-(4-Methoxyphenyl)-1-piperazinyl]-propoxy]phenyl]-1H-benzimidazole;
2-[4-[3-[4-(3-Chlorophenyl)-1-piperazinyl]-propoxy]phenyl]-1H-benzimidazole;
2-[4-[3-[4-(2,3-Dichlorophenyl)-1-piperazinyl]-propoxy]phenyl]-3H-imidazo [4,5-b]pyridine;
1-Methyl-2-[4-[3-(4-phenyl-1-piperazinyl)-propoxy]phenyl]-1H-benzimidazole;
2-[4-[4-(4-Phenyl-1-piperazinyl)-1-butynyl]-phenyl]-1H-benzimidazole;
2-[4-[4-(4-Phenyl-1-piperazinyl)butoxy]phenyl]-1H-benzimidazole;
N-[4-(1H-Benzimidazol-2-yl)phenyl]-4-phenyl-1-piperazine-3-propanamine;
4-(1H-Benzimidazol-2-yl)-N-[2-(4-phenyl-1-piperazinyl)ethyl]benzamide;
4-(1H-Benzimidazol-2-yl)-N-[2-[4-[2-(propylthio)-phenyl]-1-piperazinyl]ethyl] benzamide;
4-(1H-Benzimidazol-2-yl)-N-[2-[4-(2-methoxyphenyl)-1-piperazinyl]ethyl]benzamide;

(Z)-2-[4-[4-(4-Phenyl-1-piperazinyl)-1-butenyl]phenyl]-1H-benzimidazole; and

2-[4-[4-(4-Phenyl-1-piperazinyl)butyl]phenyl]-1H-benzimidazole;

or a pharmaceutically acceptable acid addition salt thereof.

The compounds of Formula I are valuable dopaminergic agents. Dopamine D2 antagonists are established as antipsychotic agents. More recently, the dopamine D3 receptor has been identified. On the basis of the localization of the dopamine D3 receptor in the limbic area of the brain, a selective D3 antagonist should show antipsychotic activity but not have the neurological side effects of D2 antagonists. The tests employed indicate that compounds of Formula I bind selectively to the dopamine D3 receptor. Thus, the compounds of Formula I were tested for their ability to bind to dopamine receptors as measured by their inhibition of [$^3$H]spiperone binding to the human D2 and D3 receptors in a receptor assay described by MacKenzie R. G., et al., Characterization of the human D3 dopamine receptor expressed in transfected cell lines, *Eur. J. Pharmacol.*, 266:79 (1994); and for their ability to inhibit locomotor activity in mice and rats, a measure of antipsychotic activity, according to the assay described by McLean J. R., et al., *Pharmacology, Biochemistry and Behavior*, 8:97–99 (1978). The above test methods are incorporated herein by reference. The data in Table 1 show the dopamine receptor binding activity of representative compounds of Formula I. The data in Table 2 show the locomotor activity of selected compounds of Formula I and demonstrate their utility as antipsychotic agents.

TABLE 1

Receptor Binding of Compounds of Formula I

| Example Number | Compound | Inhibition of [$^3$H]Spiperone Binding to Human D3 Receptors IC$_{50}$, nM | Inhibition of [$^3$H]Spiperone Binding to Human D2 Receptors IC$_{50}$, nM |
|---|---|---|---|
| 1 | 2-[4-[3-(4-Phenyl-1-piperazinyl)propoxy]phenyl]-1H-benzimidazole | 1.0 | 406 |
| 2 | 2-[4-[3-[2,3-Dichlorophenyl)-1-piperazinyl]propoxy]phenyl]-1H-benzimidazole | 1.7 | 45 |
| 3 | 2-[4-[3-[4-(2-Pyridinyl)-1-piperazinyl]propoxy]phenyl]-1H-benzimidazole | 8 | 70 |
| 4 | 2-[4-[3-[4-(2-Pyrimidinyl)-1-piperazinyl]propoxy]phenyl]-1H-benzimidazole | 15 | 269 |
| 5 | 2-[4-[3-[4-(4-Methylphenyl)-1-piperazinyl]propoxy]phenyl]-1H-benzimidazole | 102 | 2776 |
| 6 | 2-[4-[3-[4-(4-Fluorophenyl)-1-piperazinyl]propoxy]phenyl]-1H-benzimidazole | 16 | 119 |
| 7 | 2-[4-[3-[4-[2-(Propylthio)phenyl]-1-piperazinyl]propoxy]phenyl]-1H-benzimidazole | 1.3 | 3.7 |
| 8 | 2-[4-[3-(3,6-Dihydro-4-phenyl-1(2H)-pyridinyl)propoxy]phenyl]-1H-benzimidazole | 18 | 672 |
| 9 | 2-[4-[3-[4-(4-Chlorophenyl)-1-piperazinyl]propoxy]phenyl]-1H-benzimidazole | 27 | 784 |
| 10 | 2-[4-[3-[4-(2-Methoxyphenyl)-1-piperazinyl]propoxy]phenyl]-1H-benzimidazole | 1.7 | 8 |
| 11 | 2-[4-[3-[4-(4-Methoxyphenyl)-1-piperazinyl]propoxy]phenyl]-1H-benzimidazole | 130 | 265 |
| 12 | 2-[4-[3-[4-(3-Chlorophenyl)-1-piperazinyl]propoxy]phenyl]-1H-benzimidazole | 155 | 1271 |
| 13 | 2-[4-[3-[4-(2,3-Dichlorophenyl)-1-piperazinyl]propoxy]phenyl)-3H-imidazo[4,5-b]pyridine | 3 | 329 |
| 14 | 1-Methyl-2-[4-[3-(4-phenyl-1-piperazinyl)propoxy]phenyl]-1H-benzimidazole | 9.5 | 219 |
| 15 | 2-[4-[4-(4-Phenyl-1-piperazinyl)-1-butynyl]phenyl]-1H-benzimidazole | 1.7 | 581 |
| 16 | 2-[4-[4-(4-Phenyl-1-piperazinyl)butoxy]phenyl)-1H-benzimidazole | 1.7 | 46 |
| 17 | N-[4-(1H-Benzimidazol-2-yl)phenyl]-4-phenyl-1-piperazine-3-propanamine | 1.6 | 22 |
| 18 | 4-(1H-Benzimidazol-2-yl)-N-[2-(4-phenyl-1-piperazinyl)ethyl]benzamide | 26 | 281 |
| 19 | 4-(1H-Benzimidazol-2-yl)-N-[2-[4-[2-(propylthio)phenyl]-1-piperazinyl]ethyl]benzamide | 19 | 119 |
| 20 | 4-(1H-Benzimidazol-2-yl)-N-[2-[4-(2-methoxyphenyl)-1-piperazinyl]ethyl]benzamide | 24 | 55 |
| 21 | (Z)-2-[4-[4-(4-Phenyl-1-piperazinyl)-1-butenyl]phenyl]-1H-benzimidazole | 81 | 100 |
| 22 | 2-[4-[4-(4-Phenyl-1-piperazinyl)butyl]phenyl]-1H-benzimidazole | 1.3 | 32 |

TABLE 2

Locomotor Activity of Selected Compounds of Formula I

| Example Number | Compound | Inhibition of Locomotor Activity in Rats $ED_{50}$, mg/kg, IP |
|---|---|---|
| 1 | 2-[4-[3-(4-Phenyl-1-piperazinyl)propoxy]-phenyl]-1H-benzimidazole | 2.3 |
| 13 | 2-[4-[3-[4-(2,3-Dichlorophenyl)-1-piperazinyl]-propoxy]phenyl]-3H-imidazo[4,5-b]pyridine | 4.2 |

A compound of Formula Ia

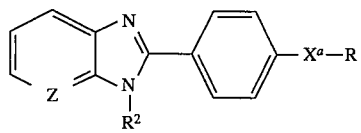

wherein R is

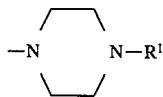

wherein $R^1$ is aryl, or heteroaryl, or

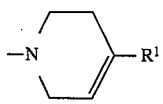

wherein $R^1$ is as defined above;
$R^2$ is H or alkyl of from 1 to 6 carbon atoms;
$X^a$ is $-Y-(CH_2)_n-$
  wherein Y is O or S and n is an integer from 2 to 5;
Z is N or CH;
and corresponding isomers thereof; or a pharmaceutically acceptable acid addition salt thereof may be prepared by reacting a compound of Formula II

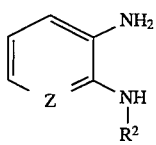

where $R^2$ and Z are as defined above with a compound of Formula III

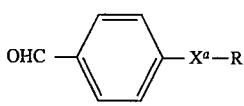

wherein R and $X^a$ is as defined above; in an oxidizing solvent such as, for example, nitrobenzene and the like at about 100° C. to about 200° C. from about 1 hour to about 24 hours. Alternatively, the reaction may be carried out in the presence of an oxidant such as, for example, sodium bisulfite or copper (II) acetate and the like in a solvent such as, for example, methanol and the like at about room temperature to about the reflux temperature of the solvent at about 2 hours to about 24 hours. Preferably, the reaction is carried out with sodium bisulfite in methanol at reflux temperature for about 6 hours.

A compound of Formula III may be prepared by reacting 4-hydroxybenzaldehyde or 4-thiohydroxybenzaldehyde with a strong base such as, for example, sodium hydride, butyllithium and the like in a solvent such as, for example, tetrahydrofuran, dimethylformamide and the like at about 0° C. to about 80° C. followed by treatment with a compound of Formula IV $$Hal-(CH_2)_n-R \qquad \text{IV}$$

wherein Hal is halogen and n and R are as defined above for about 2 hours to about 24 hours. Preferably, the reaction is carried out in dimethylformamide with sodium hydride at about 60° C. for about 6 hours. A compound of Formula Ib

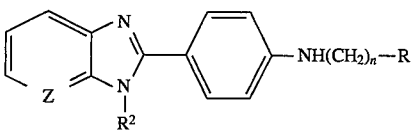

wherein R is

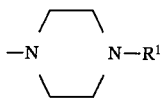

wherein $R^1$ is is as defined above, or

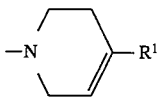

wherein $R^1$ is as defined above;
$R^2$ is H or alkyl of from 1 to 6 carbon atoms;
n is an integer from 2 to 5;
Z is N or CH;
and corresponding isomers thereof; or a pharmaceutically acceptable acid addition salt thereof may be prepared by reacting a compound of Formula Ic

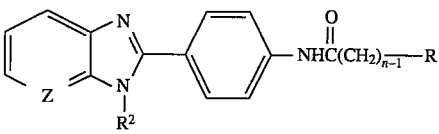

wherein R, $R^2$, Z and n are as defined above with an amide reducing agent such as, for example, lithium aluminum hydride, borane-dimethyl sulfide complex and the like in a solvent such as, for example, tetrahydrofuran and the like at about −20° C. to about the reflux temperature of the solvent at about 1 hour to about 24 hours. Preferably, the reaction is carried out with borane-dimethylsulfide complex in tetrahydrofuran at the reflux temperature of the solvent for about 2 hours.

A compound of Formula Ic may be prepared by treatment of a compound of Formula V

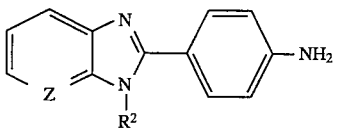

wherein $R^2$ and Z are as defined above with a compound of Formula VI

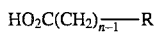 VI wherein R and n are as defined above with a peptide coupling agent such as, for example, dicyclohexylcarbodiimide, isobutylchloroformate and the like in a solvent such as, for example, dichloromethane, dimethylformamide and the like with a base such as, for example, triethylamine and the like at about −30° C. to about 50° C. for about 30 minutes to about 24 hours. Preferably, the reaction is carried out with isobutylchloroformate in dichloromethane at about −20° C. for about 4 hours with triethylamine as base.

A compound of Formula V may be prepared by reacting a compound of Formula II with 4-acetamidobenzaldehyde in nitrobenzene as solvent at about 100° C. to about 200° C. for about 1 hour to about 24 hours. Alternatively, the reaction may be carried out in the presence sodium bisulfite or copper (II) acetate in a solvent such as, for example, methanol and the like at about room temperature to about the reflux temperature of the solvent for about 2 hours to about 24 hours. Preferably, the reaction is carried out with sodium bisulfite in methanol at reflux temperature for about 6 hours. The resulting acetamide may be converted to a compound of Formula V by treatment with a strong aqueous acid such as, for example aqueous hydrochloric acid land the like at about room temperature to about reflux temperature for about 1 hour to about 6 hours. Preferably, the reaction is carried out with aqueous hydrochloric acid at about reflux temperature for about 1 hour.

A compound of Formula Id

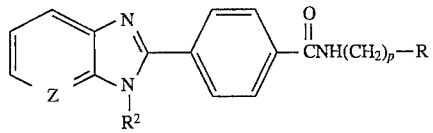 Id wherein R is

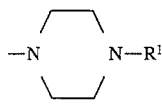

wherein $R^1$ is as defined above, or

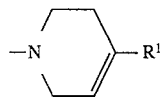

wherein $R^1$ is as defined above;
$R^2$ is H or alkyl of from 1 to 6 carbon atoms;
p is an integer from 1 to 4;
Z is N or CH;
and corresponding isomers thereof; or a pharmaceutically acceptable acid addition salt thereof may be prepared by reacting a compound of Formula VII

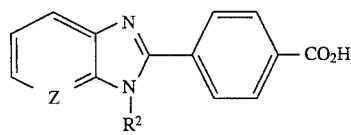 VII wherein $R^2$ and Z are as defined above with a compound of Formula VIII

 VIII wherein R and p are as defined above with a peptide coupling agent such as, for example, dicyclohexylcarbodiimide, isobutylchloroformate and the like in a solvent such as, for example, dichloromethane, dimethylformamide and the like with a base such as, for example, triethylamine and the like at about −30° C. to about 50° C. for about 30 minutes to about 24 hours. Preferably, the reaction is carried out with isobutylchloroformate in dichloromethane at about −20° C. for abut 4 hours with triethylamine as base.

A compound of Formula VII may be prepared by saponification of a compound of Formula IX

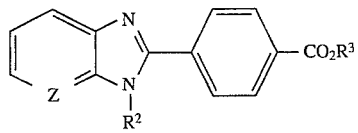 IX wherein $R^3$ is alkyl of from 1 to 6 carbon atoms and $R^2$ and Z are as defined above by treatment with an alkali metal hydroxide in a solvent such as, for example, tetrahydrofuran and the like in the presence of water at about room temperature to about the reflux temperature of the solvent for about 1 hour to about 24 hours. Preferably, the reaction is carried out with sodium hydroxide in tetrahydrofuran at the reflux temperature of the solvent for about 2 hours.

A compound of Formula IX may be prepared by reaction of a compound of Formula II with a compound of Formula X

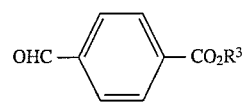 X wherein $R^3$ is as defined above in nitrobenzene as solvent at about 100° C. to about 200° C. for about 1 hour to about 24 hours. Alternatively, the reaction may be carried out in the presence of sodium bisulfite or copper (II) acetate in a solvent such as, for example, methanol and the like at about room temperature to about the reflux temperature of the solvent for about 2 hours to about 24 hours. Preferably, the reaction is carried out with sodium bisulfite in methanol at the reflux temperature of the solvent for about 6 hours.

A compound of Formula Ie

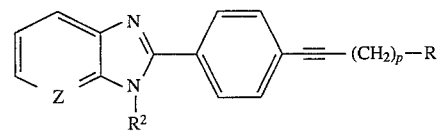 Ie wherein R is

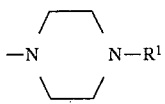

wherein $R^1$ is as defined above, or

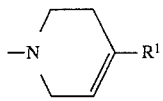

wherein $R^1$ is as defined above;
$R^2$ is H or alkyl of from 1 to 6 carbon atoms;
is an integer from 1 to 4;
Z is N or CH;
and corresponding isomers thereof; or a pharmaceutically acceptable acid addition salt thereof may be prepared by reacting a compound of Formula II with a compound of Formula XI

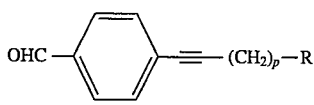

wherein R and p are as defined above in an oxidizing solvent such as, for example, nitrobenzene and the like at about 100° C. to about 200° C. for about 1 hour to about 24 hours. Alternatively, the reaction may be carried out in the presence of an oxidant such as, for example, sodium bisulfite, copper (II) acetate and the like in a solvent such as, for example, methanol and the like at about room temperature to about the reflux temperature of the solvent for about 2 hours to about 24 hours. Preferably, the reaction is carried out with sodium bisulfite in methanol at the reflux temperature of the solvent for about 6 hours.

A compound of Formula XI may be prepared by reacting 4-bromobenzaldehyde with a compound of Formula XII

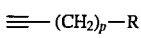 XII wherein R and p are as defined above in a solvent such as, for example, acetonitrile, dimethylformamide and the like with a transition metal catalyst such as, for example, palladium (II) acetate or bis(triphenylphosphine)palladium (II) chloride. The reaction is carried out in the presence of a copper salt and a base such as, for example, triethylamine and the like at about room temperature to about the reflux temperature of the solvent for about 1 hour to about 24 hours. Preferably, the reaction is carried out in acetonitrile with bis(triphenylphosphine)palladium (II) chloride, copper (I) iodide, and triethylamine at room temperature for about 14 hours.

A compound of Formula If

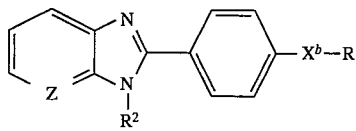 If wherein R is

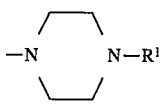

wherein $R^1$ is as defined above, or

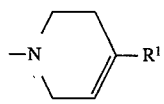

wherein $R^1$ is as defined above;
$R^2$ is H or alkyl of from 1 to 6 carbon atoms;
$X^b$ is alkyl of from 3 to 6 carbon atoms or alkenyl of from 3 to 6 carbon atoms;
Z is N or CH;
and corresponding isomers thereof; or a pharmaceutically acceptable acid addition salt thereof may be prepared by hydrogenation of a compound of Formula Ie in a solvent such as, for example, tetrahydrofuran, ethanol and the like in the presence of a catalyst such as, for example, palladium on carbon, a poisoned catalyst and the like for about 1 hour to about 24 hours. Preferably, for the preparation of the alkenes, palladium on calcium carbonate poisoned with lead is used in ethanol for about 1 hour. Preferably, for the preparation of alkanes, palladium on carbon in ethanol for 6 hours is used.

Compounds II, IV, VI, VIII, X, and XII are either known or capable of being prepared by methods known in the art.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogenerously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

2-[4-[3-(4-Phenyl-1-piperazinyl)propoxy]phenyl]-1H-benzimidazole

A mixture of 1,2-diaminobenzene (0.67 g) and 4-[3-(4-phenylpiperazin-1-yl)propoxy]benzaldehyde (Example A) (2.00 g) in nitrobenzene (65 mL) is stirred for 16 hours at 160° C. The solvent is distilled off under high vacuum and the resulting solid is purified by medium pressure liquid chromatography (MPLC) on silica gel eluting with 200:8:1 dichloromethane: ethanol:0.880 aqueous ammonia to give 0.97 g of the title compound as a tan solid; mp 240°–244° C.

In a process analogous to Example 1 using appropriate starting materials, the corresponding compounds of Formula I are prepared as follows:

EXAMPLE 2

2-[4-[3-[4-(2,3-Dichlorophenyl)-1-piperazinyl]propoxy]phenyl]-1H-benzimidazole; mp 207°–209° C.

EXAMPLE 3

2-[4-[3-[4-(2-Pyridinyl)-1-piperazinyl]propoxy]phenyl]-1H-benzimidazole; mp 218°–220° C.

EXAMPLE 4

2-[4-[3-[4-(2-Pyrimidinyl)-1-piperazinyl]propoxy]phenyl]-1H-benzimidazole; mp 222°–227° C.

EXAMPLE 5

2-[4-[3-[4-(4-Methylphenyl)-1-piperazinyl]propoxy]phenyl]-1H-benzimidazole; mp 222°–225° C.

EXAMPLE 6

2-[4-[3-[4-(4-Fluorophenyl)-1-piperazinyl]propoxy]phenyl]-1H-benzimidazole; mp 221°–224° C.

EXAMPLE 7

2-[4-[3-[4-[2-(Propylthio)phenyl]-1-piperazinyl]propoxy]phenyl]-1H-benzimidazole; mp 207°–209° C.

EXAMPLE 8

2-[4-[3-(3, 6-Dihydro-4-phenyl-1(2H)-pyridinyl)propoxy]phenyl]-1H-benzimidazole; mp 227°–232° C.

EXAMPLE 9

2-[4-[3-[4-(4-Chlorophenyl)-1-piperazinyl]propoxy]phenyl]-1H-benzimidazole; mp 241°–243° C.

EXAMPLE 10

2- [4-[3-[4- (2 -Methoxyphenyl)-1-piperazinyl]propoxy] phenyl]-1H-benzimidazole; mp 228°–230° C.

EXAMPLE 11

2- [4-[3-[4-(4-Methoxyphenyl)-1-piperazinyl]propoxy] phenyl]-1H-benzimidazole; mp 222°–224° C.

EXAMPLE 12

2- [4-[3-[4-(3-Chlorophenyl)-1-piperazinyl]propoxy]phenyl]-1H-benzimidazole; mp 221°–223° C.

EXAMPLE 13

2-[4-[3-[4-(2,3-Dichlorophenyl)-1-piperazinyl]propoxy] phenyl]-3H-imidazo[4,5-b ]pyridine; mp 229°–230° C.

EXAMPLE 14

1-Methyl-2-[4-[3-(4-phenyl-1-piperazinyl)propoxy]phenyl -1H-benzimidazole

Potassium hexamethyldisilazide (4 mL of 0.5M in toluene) is added to 2-[4-[3-(4-phenyl-1-piperazinyl)propoxy] phenyl]-1H-benzimidazole (Example 1) (0.75 g) in dimethylformamide (15 mL) at room temperature and stirred for 1 hour. Methyl iodide (0.14 mL) is added and the mixture stirred for 4 hours. Water (100 mL) is added and the mixture is extracted with dichloromethane (2×75 mL). The extracts are dried over MgSO₄, filtered and evaporated to leave a solid. This solid is purified by MPLC on silica gel eluting with 200:8:1 dichloromethane: ethanol: 0.880 aqueous ammonia to give 0.34 g of the title compound as a white solid; mp 151–154° C.

EXAMPLE 15

2-[4-[4-(4-Phenyl-1-piperazinyl)-1-butynyl]phenyl]-1H-benzimidazole

A mixture of 4-[4-(4-phenylpiperazin-1-yl)but-1-ynyl] benzaldehyde (Example B) (1.28 g), sodium bisulfite (0.4 g) and 1,2-diaminobenzene (0.43 g) is stirred in methanol (50 mL) at reflux for 18 hours. The mixture is filtered and the solvent evaporated. The residue is purified by chromatography on silica gel eluting with 200:8:1 dichloromethane:ethanol:0.880 aqueous ammonia to give 0.70 g of the title compound as a tan solid; mp 247°–248° C.

EXAMPLE 16

2-[4-[4-(4-Phenyl-1-piperazinyl)butoxy]phenyl]-1H-benzimidazole

A mixture of 2-[4-(4-chlorobutoxy) phenyl]-1H-benzimidazole (Example C) (0.25 g) and 1-phenylpiperazine (0.70 g) is stirred at 110° C. in dimethylformamide (20 mL) for 6 hours. The solvent is evaporated and the residue is purified by chromatography on silica gel eluting with 100:8:1 dichloromethane: ethanol: 0.880 aqueous ammonia to give 0.15 g of the title compound as a brown solid; mp 193°–196° C.

EXAMPLE 17

N-[4-(1H-Benzimidazol-2-yl)phlenyl]-4-phenyl-1-piperazine-3-propanamine

A mixture of [4-(1-benzyl-1H-benzimidazol-2-yl)phenyl] -[3-(4-phenylpiperazin-1-yl)propyl] amine (Example D) (0.29 g) , 10% palladium on carbon (0.3 g) and ammonium formate (0.18 g) is stirred in methanol (10 mL) at reflux under nitrogen for 5 hours. The mixture is filtered through Celite and evaporated. The residue is purified by MPLC on silica gel eluting with 200:8:1 dichloromethane: ethanol: 0.880 aqueous ammonia to give 0.14 g of the title compound as a yellow solid; mp 231°–234° C.

EXAMPLE 18

4-(1H-Benzimidazol-2-yl)-N-[2-(4-phenyl-1-piperazinyl)ethyl]benzamide

A mixture of 4-(1H-benzimidazol-2-yl)benzoic acid (Example E) (0.50 g), 2-(4-phenylpiperazin-1-yl)ethylamine (0.77 g), 1-(3-dimethylaminopropyl)3-ethylcarbodiimide hydrochloride (0.44 g) and triethylamine (0.29 mL) in dichloromethane (20 mL) is stirred at room temperature for 2 days. The mixture is washed with water (50 mL), dried over MgSO$_4$, filtered and evaporated. The residue is purified by MPLC on silica gel eluting with 100:8:1 dichloromethane: ethanol:0.880 aqueous ammonia to give 0.33 g of the title compound as a beige solid; mp 190°–192° C.

In a process analogous to Example 18 using appropriate starting materials, the corresponding compounds of Formula I are prepared as follows:

EXAMPLE 19

4-(1H-Benzimidazol-2-yl)-N-[2-[4-[2-(propylthio)phenyl]-1-piperazinyl]ethyl]benzamide; mp 205°–207° C.

EXAMPLE 20

4-(1H-Benzimidazo]-2-yl)-N-[2-[4-(2-methoxyphenyl)-1-piperazinyl]ethyl]benzamide; mp 243°–244° C.

EXAMPLE 21

(Z)-2-[4-[4-(4-Phenyl-1-piperazinyl)-1-butenyl]phenyl]-1H-benzimidazole

A mixture of 2-(4-bromophenyl)-1H-benzimidazole (Example F) (8.08 g), 1-but-3-enyl-4-phenylpiperazine (Example G) (8.0 g), palladium acetate (0.66 g), tri-o-tolylphosphine (1.8 g) and triethylamine (7.05 g) in acetonitrile (100 mL) is stirred at reflux for 2 hours. The mixture is cooled and filtered through Celite. The filtrate is evaporated to leave a brown solid. This solid is purified by MPLC on silica gel eluting with 100:8:1 dichloromethane: ethanol: 0.880 aqueous ammonia to give 1.84 g of the title compound as a white solid; mp 140°–145° C.

EXAMPLE 22

2-[4-[4-(4-Phenyl-1-piperazinyl)butyl]phenyl]1H-benzimidazole (Z)-2-[4-[4-(4-Phenyl-1-piperazinyl)-1-butenyl]phenyl]-1H-benzimidazole (Example 21) (0.5 g) is hydrogenated with 5% palladium on carbon (0.1 g) in methanol (10 mL) and filtered. The filtrate is evaporated and the residue is purified by MPLC on silica gel eluting with 100:8:1 dichloromethane: ethanol:0.880 aqueous ammonia to give 0.31 g of the title compound as a white solid; mp 239°–243° C.

PREPARATION OF STARTING MATERIALS

EXAMPLE A

Preparation of 4-[3-[4-Phenylpiperazin-1-yl)propoxy] benzaldehyde

Step A: Preparation of 1-(3-Chloropropyl)-4-phenylpiperazine

1-Phenylpipezazine (100 g) is added dropwise to 1-bromo-3-chloropropane (49 g) in diethyl ether (30 mL) and dichloromethane (100 mL). The mixture is stirred at 50° C. for 4 hours. The mixture is filtered and the filtrate is extracted with 2N hydrochloric acid (3×300 mL). The extracts are basified with potassium carbonate and extracted with dichloromethane (3×300 mL). The extracts are dried over magnesium sulfate, filtered and evaporated to leave a brown oil. This oil is distilled at 135°–160° C./0.4 mm Hg to give 24.4 g of the title compound as a clear, colorless oil.

Step B: Preparation of 4-[3-(4-Phenylpiperazin-1-yl)propoxy]benzaldehyde

Sodium hydride (3.59 g of 60% in oil) is added to 4-hydroxybenzaldehyde (9.95 g) in dimethylformamide (250 mL) and the mixture stirred at 60° C. for 30 minutes. 1-(3-Chloropropyl)-4-phenylpiperazine (Step A) (19.5 g) is added and the mixture stirred for 14 hours at 60° C. The solvent is evaporated and the residue treated with water (300 mL) and extracted with dichloromethane (3×150 mL). The extracts are dried over magnesium sulfate, filtered and evaporated to leave a beige solid. This solid is recrystallized from ethyl acetate/diethyl ether to give 18.4 g of the title compound as a light beige solid.

EXAMPLE B

Preparation of 4-[4-(4-Phenylpiperazin-1-yl) but-1-ynyl] benzaldehyde

Step A: Preparation of 1-But-3-ynyl-4-phenylpiperazine

A mixture of but-3-ynyl-p-toluenesulfonate (8.97 g), 1-phenylpiperazine (6.49 g) and sodium bicarbonate (3.7 g) in dimethylformamide (100 mL) is stirred at 80° C. for 14 hours. The solvent is evaporated and the residue dissolved in dichloromethane, washed with water and dried over MgSO$_4$. The solution is filtered through silica gel and the product eluted with 10% ethyl acetate/hexanes to give 6.76 g of the title compound as a white solid.

Step B: Preparation of 4-[4-(4-Phenylpiperazin-1-yl)but-1-ynyl]benzaldehyde

A mixture of 4-bromobenzaldehyde (4.05 g), 1-but-3-ynyl-4-phenylpiperazine (Step A) (4.69 g), triethylamine (9.2 mL), bis (triphenylphosphine)palladium dichloride (0.31 g) and copper (I) iodide (0.08 g) in acetonitrile (100 mL) is degassed with nitrogen and stirred at room temperature for 16 hours. The solvent is evaporated and the residue is dissolved in dichloromethane (200 mL), washed with 2N sodium carbonate (150 mL), dried over MgSO$_4$, filtered and evaporated to leave a brown oil. This oil is purified by MPLC on silica gel eluting with 15% then 30% ethyl acetate (EtOAc)/hexanes to give 4.2 g of the title compound as a yellow waxy solid.

EXAMPLE C

Preparation of 2-[4-(4-Chlorobutoxy)phenyl]-1H-benzimidazole

Step A: Preparation of 4-(4-Chlorobutoxy)benzaldehyde

4-Hydroxybenzaldehyde (26.4 g) in dimethylformamide (50 mL) is added to sodium hydride (8.64 g of 60% in oil) in dimethylformamide (200 mL). 1-Bromo-3-chloropropane (93.2 g) is added and the mixture stirred at 60° C. for 3 hours. The mixture is poured into water (400 mL) and extracted with diethyl ether (3×150 mL). The extracts are dried over MgSO$_4$, filtered and evaporated to leave an orange oil. The oil is distilled end 40.7 g of the title compound collected at 158°–175° C./0.7 mmHg as a yellow oil.

Step B: Preparation of 2-[4-(4-Chlorobutoxy)phenyl]-1H-benzimidazole

A mixture of copper (II) acetate monohydrate (7.76 g), 1,2-diaminobenzene (2.10 g), 4-(4-chlorobutoxy]benzaldehyde (Step A) (5.0 g) is slowly heated to reflux in water (10 mL) and methanol (100 mL) and stirred at reflux for 1 hour. The mixture is cooled and a brown precipitate filtered off. The precipitate is suspended in methanol (100 mL) and hydrogen sulfide bubbled through for 30 minutes followed by nitrogen. The mixture is heated to reflux, cooled and filtered. All the filtrates are combined and 0.880 ammonium hydroxide added until just basic. The filtrates are diluted with an equal volume of water and the resulting pale-grey precipitate collected. The precipitate is recrystallized from methanol/water to give 3.8 g of the title compound.

EXAMPLE D

Preparation of [4-(1-Benzyl-1H-benzimidazol-2-yl)-phenyl]-[3-(4-phenylpiperazin-1-yl) propyl]amine Step A: Preparation of 4-(1-Benzyl-1H-benzimidazol-2-yl)-phenylamine Benzyl-(2-nitrophenyl)amine (20 g) is hydrogenated with Raney nickel in methanol (600 mL) and filtered. The filtrate is added to 4-acetamidobenzaldehyde (14.3 g) and sodium bisulfite (9.3 g)in methanol (200 mL) and the mixture stirred at reflux for 8 hours. The mixture is filtered and evaporated to leave a brown foam. This foam is stirred at reflux in concentrated hydrochloric acid (200 mL) and water (300 mL) for 3 hours. The cooled mixture is basified with 25% sodium hydroxide. The mixture is extracted with dichloromethane (2×200 mL), the extracts dried over MgSO$_4$, filtered and evaporated to leave a brown oil. The oil is diluted with ethyl acetate to precipitate a brown solid which is recrystallized from ethyl acetate/diethyl ether to give 8.3 g of the title compound as a brown solid.

Step B: Preparation of N-[4-(1-Benzyl-1H-benzimidazol-2-yl)phenyl]-3-(4-phenylpiperazin-1-yl) propionamide i-Butylchloroformate (0.24 mL) is added to 4-phenylpiperazin-1-ylpropanoic acid (0.39 g) and triethylamine (0.28 mL) in dichloromethane (10 mL) at −20° C. under nitrogen. After stirring for 30 minutes, 4-(1-benzyl-1H-benzimidazol-2-yl)phenylamine (Step A) (0.50 g) in dichloromethane (10 mL) is added dropwise at −20° C. and the mixture allowed to warm to room temperature with stirring. The mixture is diluted with dichloromethane (50 mL), washed with 2N sodium carbonate (50 mL), dried over MgSO$_4$, filtered and evaporated to leave a yellow oil. This oil is purified by MPLC on silica gel eluting with 250:8:1 dichloromethane: ethanol: 0.880 aqueous ammonia to give 0.66 g of the title compound as a yellow foam.

Step C: Preparation of [4-(1-Benzyl-1H-benzimidazol-2-yl)phenyl]-[3-(4-phenylpiperazin-1-yl) propyl]amine Borane.THF (3.5 mL of 1.0M in tetrahydrofuran (THF)) is added to N-[4-(1-benzyl-1H-benzimidazol-2yl)phenyl -3-(4-phenylpiperazin-1-yl) propionamide (Step B) (0.45 g) in THF (10 mL) and the mixture stirred at reflux for 2 hours. 2N Hydrochloric acid (5 mL) is added and the mixture stirred for 30 minutes. The solvent is evaporated and the residue treated with 2N sodium carbonate (100 mL). The mixture is extracted with dichloromethane (3×50 mL) and the extracts are dried over MgSO$_4$, filtered and evaporated to leave a yellow oil. This oil is purified by MPLC on silica gel eluting with 300:8:1 dichloromethane: ethanol: 0.880 aqueous ammonia to give 0.31 g of the title compound as a white solid.

EXAMPLE E

Preparation of 4-(1H-Benzimidazol-2-yl)benzoic acid

Step A: Preparation of Methyl 4-(1H-benzimidazol-2-yl)benzoate

A mixture of 1,2-diaminobenzene (6.59 g), methyl 4-formylbenzoate (10.0 g) and sodium bisulfite (6.60 g) in methanol (500 mL) is stirred at reflux for 6 hours. The mixture is filtered and the solvent evaporated to leave a yellow solid. This solid is recrystallized from ethyl acetate/ethanol to give 2.92 g of the title compound as an oil-white solid.

Step B: Preparation of 4-(1H-Benzimidazol-2-yl)benzoic acid

Methyl 4-(1H-benzimidazol-2-yl)benzoate (Step A) (2.63 g) is stirred in THF (50 mL) and water (10 mL) with sodium hydroxide (2.08 g) at reflux for 4 hours. The solvent is evaporated and the residue treated with 2N hydrochloric acid (100 mL). The resulting suspension is collected, washed with methanol/ethyl acetate and dried to give 2.52 g of the title compound as a white solid.

EXAMPLE F

Preparation of 2-(4-Bromophenyl)-1H-benzimidazole

Sodium bisulfite (14.4 g) is added to 4-bromobenzaldehye (17.1 g) in ethanol (100 mL) and the mixture stirred at reflux for 15 minutes. 1,2-Diaminobenzene (10 g) is added and the mixture stirred at reflux for 16 hours. The solvent is evaporated and the residue is washed with water and ethanol to afford 18.0 g of the title compound as a beige solid.

EXAMPLE G

Preparation of 1-But-3-enyl-4-phenylpiperazine

A mixture of 4-bromobut-1-ene (8.68 g) and 1-phenylpiperazine (35.7 g) is heated to reflux in diethyl ether (100 mL) for 2 hours. The mixture is filtered and the filtrate is extracted with 2N hydrochloric acid (150 mL). The extracts are washed with diethyl ether (150 mL) and basified with 25% sodium hydroxide. The aqueous layer is extracted with diethyl ether (3×100 mL), the extracts dried over $MgSO_4$, filtered and evaporated to leave a brown oil. This oil is purified by MPLC on silica gel eluting with 5% methanol in dichloromethane to give 10.4 g of the title compound as a yellow oil.

We claim:
1. A compound of Formula I

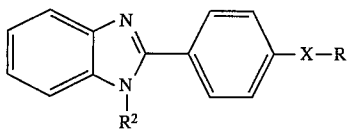

wherein R is

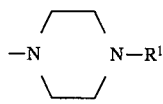

wherein $R^1$ is aryl, or heteroaryl;
$R^2$ is hydrogen, or alkyl of from 1 to 6 carbon atoms;
X is -Y- $(CH_2)_n$-
   wherein Y is O, S or NH, and n is an integer from 2 to 5,

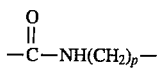

wherein p is an integer from 1 to 4,

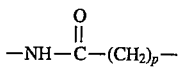

wherein p is as defined above,
alkyl of from 3 to 6 carbon atoms,
alkenyl of from 3 to 6 carbon atoms,
alkynyl of from 3 to 6 carbon atoms;
and corresponding cis or trans isomers or mixtures of cis and trans isomers thereof; or a pharmaceutically acceptable acid addition salt thereof.

2. A compound according to claim 1,
wherein R is

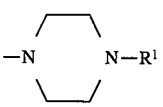

wherein $R^1$ is aryl, or heteroaryl;
$R^2$ is hydrogen,
   methyl, or
   ethyl;
X is -Y- $(CH_2)_n$-
   wherein Y is O or NH and n is an integer from 3 to 4,

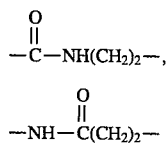

butyl,
butenyl, or
butynyl.

3. A compound selected from the group consisting of:
2-[4-[3-(4-Phenyl-1-piperazinyl)propoxy]-phenyl]benzimidazole;
2-[4-[3-[4-(2,3-Dichlorophenyl)-1-piperazinyl]propoxy] phenyl]-1H-benzimidazole;
2-[4-[3-[4-(2-Pyridinyl)-1-piperazinyl]propoxy]phenyl] 1H-benzimidazole;
2-[4-[3-[4-(2-Pyrimidinyl)-1-piperazinyl]propoxy]phenyl]-1H-benzimidazole;
2-[4-[3-[4-(4-Methylphenyl)-1-piperazinyl]propoxy]phenyl]-1H-benzimidazole;
2-[4-[3-[4-(4-Fluorophenyl)-1-piperazinyl]propoxy]phenyl]-1H-benzimidazole;
2-[4-[3-[4-[2-(Propylthio)phenyl]-1-piperazinyl]propoxy] phenyl]-1H-benzimidazole;
2-[4-[3-[4-(4-Chlorophenyl)-1-piperazinyl]propoxy]phenyl]-1H-benzimidazole;
2-[4-[3-[4-(2-Methoxyphenyl)-1-piperazinyl]propoxy]phenyl]1H-benzimidazole;
2-[4-[3-[4-(4-Methoxyphenyl)-1-piperazinyl]propoxy]phenyl]-1H-benzimidazole;
2-[4-[3-[4-(3-Chlorophenyl)-1-piperazinyl]propoxy phenyl]-1H-benzimidazole;
2-[4-[3-[4-(2,3-Dichlorophenyl)-1-piperazinyl]propoxy] phenyl]-3H-imidazo-[4,5b]pyridine:
1-Methyl-2-[4-[3-(4-phenyl-1-piperazinyl)propoxy]phenyl]-1H-benzimidazole;
2-[4-[4-(4-Phenyl-1-piperazinyl)-1-butynyl]phenyl]-1H-benzimidazole;
2-[4-[4-(4-Phenyl-1-piperazinyl)butoxy]phenyl]-1H-benzimidazole;
N-[4-(1H-Benzimidazol-2-yl)phenyl]-4-phenyl-1-piperazine-3-propanamine;
4-(1H-Benzimidazol-2-yl)-N-[2-(4-phenyl-1-piperazinyl)ethyl]benzamide;
4-(1H-Benzimidazol-2-yl)-N-[2-[4-[2-(propylthio)phenyl]-1-piperazinyl]ethyl]-benzamide;
4-(1H-Benzimidazol-2-yl)-N-[2-[4-(2-methoxyphenyl)-1-piperazinyl]ethyl]benzamide;
(Z)-2-[4-[4-(4-Phenyl-1-piperazinyl)-1-butenyl]phenyl]-1H-benzimidazole; and
2-[4-[4-(4-Phenyl-1-piperazinyl)butyl]phenyl]-1-H-benzimidazole.

4. A pharmaceutical composition adapted for administration as an agent for treating schizophrenia comprising a therapeutic effective amount of a compound according to claim 1 in admixture with a pharmaceutically acceptable excipient, diluent, or carrier.

5. A method of treating schizophrenia comprising administering to a host suffering therefrom a therapeutic effective amount of a compound of Formula I

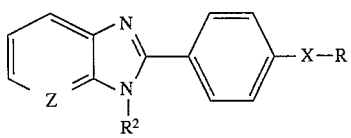

wherein R is

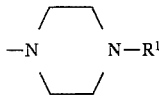

wherein R¹ is aryl, or heteroaryl;

R² is hydrogen, or alkyl of from 1 to 6 carbon atoms;

X is -Y- (CH$_2$)$_n$- wherein Y is O, S or NH, and n is an integer from 2 to 5,

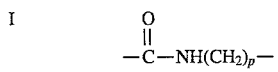

wherein p is an integer from 1 to 4,

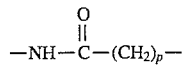

wherein p is as defined above,
alkyl of from 3 to 6 carbon atoms,
alkenyl of from 3 to 6 carbon atoms,
alkynyl of from 3 to 6 carbon atoms;

Z is N or CH;

and corresponding cis or trans isomers or mixtures of cis and trans isomers thereof; or a pharmaceutically acceptable acid addition salt thereof in unit dosage form.

* * * * *

UNITED STATES PATENT AND TRADEMARK OFFICE
CERTIFICATE OF CORRECTION

PATENT NO. : 5,486,517  
DATED : January 23, 1996  
INVENTOR(S) : Downing, et al.

Page 1 of 2

It is certified that error appears in the above-indentified patent and that said Letters Patent is hereby corrected as shown below:

Column 19, line 34, insert space between "to" and "5,".

Column 20, line 13, before "benzimi-" insert -- -1H- --.

Column 20, line 15, insert hyphen at the end of the line.

Column 20, line 26, insert hyphen at the end of the line.

Column 20, line 32, insert hyphen before "1H".

Column 20, line 35, insert bracket after "propoxy".

Column 20, line 37, insert hyphen at the end of the line.

Column 20, line 38, insert hyphen between "5" and "b".

Column 20, line 38, delete colon at the end of the line and insert semicolon instead.

Column 20, line 49, insert hyphen before "ethyl]".

UNITED STATES PATENT AND TRADEMARK OFFICE
CERTIFICATE OF CORRECTION

PATENT NO. : 5,486,517
DATED : January 23, 1996
INVENTOR(S) : Downing, et al.

It is certified that error appears in the above-indentified patent and that said Letters Patent is hereby corrected as shown below:

Column 20, line 57, delete the hyphen between "1" and "H" and close up the space.

Signed and Sealed this

Fifth Day of November, 1996

*Attest:*

BRUCE LEHMAN

*Attesting Officer*  *Commissioner of Patents and Trademarks*